United States Patent [19]
Ostler

[11] Patent Number: 6,116,900
[45] Date of Patent: Sep. 12, 2000

[54] BINARY ENERGIZER AND PEROXIDE DELIVERY SYSTEM FOR DENTAL BLEACHING

[75] Inventor: Calvin D. Ostler, Riverton, Utah

[73] Assignee: LumaChem, Inc., West Jordan, Utah

[21] Appl. No.: 09/190,913

[22] Filed: Nov. 12, 1998

Related U.S. Application Data

[60] Provisional application No. 60/065,924, Nov. 17, 1997.

[51] Int. Cl.[7] ............................................. A61C 5/04
[52] U.S. Cl. .................................. 433/89; 433/215
[58] Field of Search ............................ 433/89, 90, 215, 433/217.1, 80

[56] References Cited

U.S. PATENT DOCUMENTS

| | | | |
|---|---|---|---|
| Re. 31,279 | 6/1983 | Mefferd et al. | 372/107 |
| Re. 34,196 | 3/1993 | Munro | 433/215 |
| 2,754,590 | 7/1956 | Cohen | 433/90 |
| 3,605,039 | 9/1971 | Harris et al. | 331/94.5 |
| 3,763,442 | 10/1973 | McMahan | 331/94.5 |
| 3,801,202 | 4/1974 | Breaux | 356/85 |
| 3,931,589 | 1/1976 | Aisenberg et al. | 331/94.5 |

(List continued on next page.)

*Primary Examiner*—John J. Wilson
*Attorney, Agent, or Firm*—Daniel McCarthy

[57] ABSTRACT

A dental bleach storage, mixing and delivery device and related method are disclosed. The device includes a barrel with at least two chambers. The chambers store components that when mixed can form a dental bleach or whitener. A plunger is provided that can be reciprocated within the barrel to force such components from their chambers. A mixing tip is provided for the end of the barrel. The components may be forced through the mixing tip which thoroughly mixes them together. The resulting bleach or whitener is applied to a patient's teeth where oxygen ions released from the bleach or whitener and will whiten the patient's teeth.

8 Claims, 1 Drawing Sheet

U.S. PATENT DOCUMENTS

| | | | |
|---|---|---|---|
| 3,943,046 | 3/1976 | De Sorga et al. | 204/159.23 |
| 3,962,656 | 6/1976 | Peressini | 331/94.5 PE |
| 3,967,214 | 6/1976 | Thatcher | 331/94.5 |
| 3,970,962 | 7/1976 | Peressini et al. | 331/94.5 PE |
| 4,007,430 | 2/1977 | Fletcher et al. | 331/94.5 D |
| 4,053,845 | 10/1977 | Gould | 330/4.3 |
| 4,061,986 | 12/1977 | Barker | 331/94.5 |
| 4,161,436 | 7/1979 | Gould | 204/157.1 R |
| 4,191,622 | 3/1980 | Phillips et al. | 204/159.22 |
| 4,203,080 | 5/1980 | Wright et al. | 331/94.5 D |
| 4,224,525 | 9/1980 | Phillips et al. | 250/531 |
| 4,240,415 | 12/1980 | Haynie | 433/216 |
| 4,280,536 | 7/1981 | Dumond et al. | 372/82 |
| 4,298,005 | 11/1981 | Mutzhas | 128/396 |
| 4,329,421 | 5/1982 | Wisnosky et al. | 430/322 |
| 4,411,931 | 10/1983 | Duong | 427/54.1 |
| 4,447,151 | 5/1984 | McLellan et al. | 356/218 |
| 4,477,901 | 10/1984 | McMahan | 372/64 |
| 4,479,225 | 10/1984 | Mohler et al. | 372/97 |
| 4,522,593 | 6/1985 | Fischer | 433/136 |
| 4,551,100 | 11/1985 | Fischer | 433/218 |
| 4,573,159 | 2/1986 | Aagano et al. | 372/34 |
| 4,578,055 | 3/1986 | Fischer | 604/2 |
| 4,582,701 | 4/1986 | Piechota, Jr. | 424/52 |
| 4,611,327 | 9/1986 | Clark et al. | 372/58 |
| 4,613,972 | 9/1986 | Bettman | 372/101 |
| 4,615,033 | 9/1986 | Nakano et al. | 372/99 |
| 4,615,034 | 9/1986 | von Gunten et al. | 372/99 |
| 4,625,317 | 11/1986 | Kolb et al. | 372/88 |
| 4,635,272 | 1/1987 | Kamide et al. | 372/87 |
| 4,656,635 | 4/1987 | Baer et al. | 372/27 |
| 4,661,070 | 4/1987 | Friedman | 433/203.1 |
| 4,665,524 | 5/1987 | Cotter | 372/18 |
| 4,674,092 | 6/1987 | Cannon | 372/33 |
| 4,687,663 | 8/1987 | Schaeffer | 424/52 |
| 4,696,010 | 9/1987 | Eastman | 372/34 |
| 4,697,269 | 9/1987 | Ohara | 372/34 |
| 4,698,835 | 10/1987 | Ono et al. | 378/136 |
| 4,704,583 | 11/1987 | Gould | 330/4.3 |
| 4,713,825 | 12/1987 | Adsett | 372/107 |
| 4,716,569 | 12/1987 | Bees | 372/38 |
| 4,723,257 | 2/1988 | Baer et al. | 372/108 |
| 4,727,554 | 2/1988 | Watanabe | 372/36 |
| 4,769,824 | 9/1988 | Seki | 372/107 |
| 4,784,135 | 11/1988 | Blum et al. | 128/303.1 |
| 4,817,096 | 3/1989 | Nighan et al. | 372/5 |
| 4,862,469 | 8/1989 | Couillaud et al. | 372/33 |
| 4,872,936 | 10/1989 | Engelbrecht | 156/307 |
| 4,877,401 | 10/1989 | Higuchi et al. | 433/215 |
| 4,887,271 | 12/1989 | Taylor | 372/29 |
| 4,895,517 | 1/1990 | Fischer | 433/244 |
| 4,896,330 | 1/1990 | Krueger et al. | 372/65 |
| 4,904,872 | 2/1990 | Grix et al. | 250/423 |
| 4,941,873 | 7/1990 | Fischer | 604/54 |
| 4,968,251 | 11/1990 | Darnell | 433/216 |
| 4,971,556 | 11/1990 | Ritano | 433/102 |
| 4,983,380 | 1/1991 | Yarborough | 424/52 |
| 4,983,381 | 1/1991 | Torres Zaragoza | 424/53 |
| 4,989,217 | 1/1991 | Ostler | 372/107 |
| 4,990,089 | 2/1991 | Munro | 433/215 |
| 4,995,540 | 2/1991 | Colin et al. | 433/90 |
| 5,002,854 | 3/1991 | Fan et al. | 430/270 |
| 5,002,855 | 3/1991 | Fan et al. | 430/270 |
| 5,005,181 | 4/1991 | Yoshioka et al. | 372/59 |
| 5,007,737 | 4/1991 | Hirleman, Jr. | 356/336 |
| 5,007,837 | 4/1991 | Werly | 433/226 |
| 5,009,885 | 4/1991 | Yarborough | 424/53 |
| 5,031,768 | 7/1991 | Fischer | 206/370 |
| 5,032,178 | 7/1991 | Cornell | 106/35 |
| 5,033,650 | 7/1991 | Colin et al. | 433/90 |
| 5,040,182 | 8/1991 | Spinelli et al. | 372/18 |
| 5,041,280 | 8/1991 | Smigel | 424/52 |
| 5,055,743 | 10/1991 | Ekstrand | 315/111.51 |
| 5,098,299 | 3/1992 | Fischer | 433/215 |
| 5,098,303 | 3/1992 | Fischer | 433/215 |
| 5,123,845 | 6/1992 | Vassilladis et al. | 433/215 |
| 5,127,730 | 7/1992 | Brelje et al. | 356/318 |
| 5,149,659 | 9/1992 | Hakuta et al. | 666/691 |
| 5,154,861 | 10/1992 | McBrierty et al. | 662/854 |
| 5,175,077 | 12/1992 | Grossa | 430/327 |
| 5,181,214 | 1/1993 | Berger et al. | 372/34 |
| 5,181,215 | 1/1993 | Sam et al. | 372/34 |
| 5,214,658 | 5/1993 | Ostler | 372/23 |
| 5,238,744 | 8/1993 | Williams et al. | 428/412 |
| 5,246,371 | 9/1993 | Fischer | 433/217 |
| 5,254,114 | 10/1993 | Reed, Jr. et al. | 606/15 |
| 5,269,684 | 12/1993 | Fischer | 433/90 |
| 5,275,564 | 1/1994 | Vassilliadis et al. | 433/226 |
| 5,280,536 | 1/1994 | Dumond et al. | 372/82 |
| 5,286,257 | 2/1994 | Fischer | 604/82 |
| 5,289,919 | 3/1994 | Fischer | 206/571 |
| 5,290,259 | 3/1994 | Fischer | 604/218 |
| 5,306,143 | 4/1994 | Levy | 433/29 |
| 5,318,562 | 6/1994 | Levy et al. | 606/16 |
| 5,321,715 | 6/1994 | Trost | 372/69 |
| 5,324,200 | 6/1994 | Vassilladis et al. | 433/224 |
| 5,328,462 | 7/1994 | Fischer | 604/82 |
| 5,332,092 | 7/1994 | Fischer | 206/365 |
| 5,349,591 | 9/1994 | Weston et al. | 372/25 |
| 5,356,291 | 10/1994 | Darnell | 433/216 |
| 5,360,834 | 11/1994 | Popall et al. | 522/36 |
| 5,364,267 | 11/1994 | Fischer | 433/26 |
| 5,376,006 | 12/1994 | Fisher | 433/215 |
| 5,387,103 | 2/1995 | Fischer | 433/89 |
| 5,409,631 | 4/1995 | Fischer | 252/186.25 |
| 5,425,641 | 6/1995 | Fischer | 433/226 |
| 5,425,953 | 6/1995 | Sintov et al. | 424/404 |
| 5,445,523 | 8/1995 | Fischer et al. | 433/90 |
| 5,464,348 | 11/1995 | Fischer et al. | 433/26 |
| 5,467,362 | 11/1995 | Mrrray | 372/5 |
| 5,472,991 | 12/1995 | Schmitt et al. | 522/4 |
| 5,478,235 | 12/1995 | Schuldt et al. | 433/37 |
| 5,501,579 | 3/1996 | Kimura et al. | 417/269 |
| 5,501,599 | 3/1996 | Rechmann | 433/215 |
| 5,534,562 | 7/1996 | Jensen et al. | 523/118 |
| 5,550,853 | 8/1996 | Ostler | 372/34 |
| 5,558,230 | 9/1996 | Fsicher et al. | 226/570 |
| 5,575,655 | 11/1996 | Darnell | 433/216 |
| 5,603,701 | 2/1997 | Fischer | 604/211 |
| 5,611,687 | 3/1997 | Wagner | 433/80 |
| 5,618,273 | 4/1997 | Fischer | 604/211 |
| 5,632,739 | 5/1997 | Anderson et al. | 606/2 |
| 5,635,162 | 6/1997 | Fischer | 424/49 |
| 5,643,206 | 7/1997 | Fischer | 604/82 |
| 5,645,428 | 7/1997 | Yarborough | 433/215 |
| 5,665,066 | 9/1997 | Fischer | 604/82 |
| 5,667,386 | 9/1997 | Black et al. | 433/213 |
| 5,685,712 | 11/1997 | Fischer | 433/26 |
| 5,692,900 | 12/1997 | Fischer | 433/26 |
| 5,697,903 | 12/1997 | Fischer | 604/82 |
| 5,697,918 | 12/1997 | Fischer et al. | 604/227 |
| 5,700,148 | 12/1997 | Fischer et al. | 433/217.01 |
| 5,708,052 | 1/1998 | Fischer et al. | 523/116 |
| 5,722,829 | 3/1998 | Wilcox et al. | 433/90 |
| 5,722,833 | 3/1998 | Fischer et al. | 433/217.1 |
| 5,725,843 | 3/1998 | Fischer | 424/49 |
| 5,746,598 | 5/1998 | Fischer | 433/216 |
| 5,766,011 | 7/1998 | Sibner | 433/215 |
| 5,770,105 | 6/1998 | Fischer | 252/186.25 |
| 5,770,182 | 6/1998 | Fischer | 424/49 |
| 5,775,904 | 7/1998 | Riitano | 433/102 |
| 5,776,127 | 7/1998 | Anderson et al. | 606/2 |

| | | | |
|---|---|---|---|
| 5,785,955 | 7/1998 | Fischer | 424/49 |
| 5,800,163 | 9/1998 | Rueggeberg et al. | 433/9 |
| 5,803,734 | 9/1998 | Knutson | 433/136 |
| 5,816,804 | 10/1998 | Fischer | 433/90 |
| 5,846,058 | 12/1998 | Fischer | 433/216 |
| 5,851,512 | 12/1999 | Fischer | 424/49 |
| 5,855,870 | 1/1999 | Fischer | 424/49 |
| 5,858,332 | 1/1999 | Jensen et al. | 424/53 |
| 5,860,806 | 1/1999 | Pranitis, Jr. et al. | 433/80 |
| 5,868,769 | 2/1999 | Rosenblood et al. | 606/161 |
| 5,882,201 | 3/1999 | Salem | 443/216 |
| 5,890,900 | 4/1999 | Fischer et al. | 433/149 |
| 5,890,901 | 4/1999 | Fischer et al. | 433/149 |
| 5,922,307 | 7/1999 | Montgomery | 424/53 |
| 5,947,278 | 9/1999 | Sawhney et al. | 206/216 |
| 5,967,778 | 10/1999 | Riitano | 433/77 |
| 5,985,249 | 11/1999 | Fischer | 424/49 |
| 6,008,264 | 12/1999 | Ostleret et al. | 522/4 |

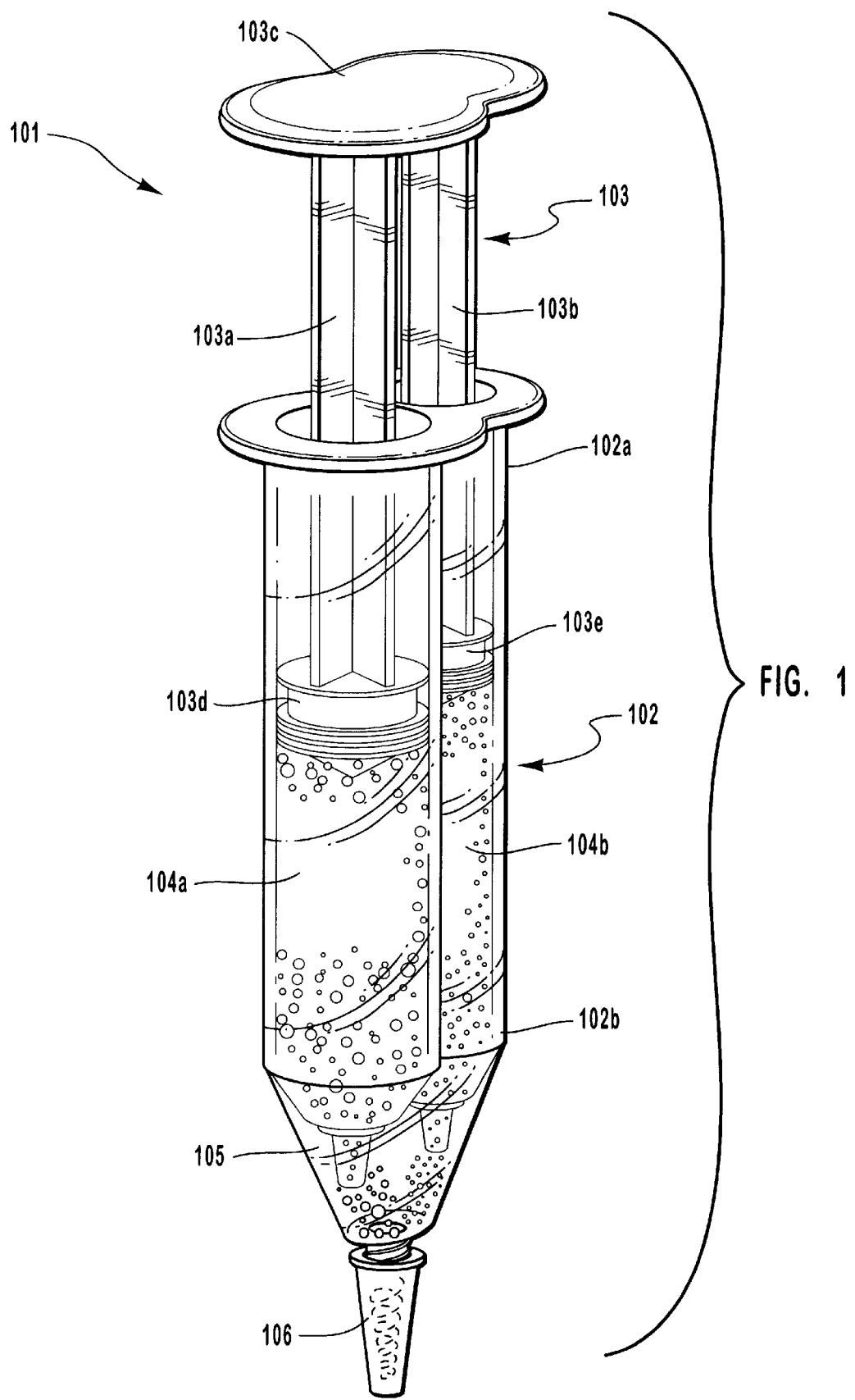

BINARY ENERGIZER AND PEROXIDE DELIVERY SYSTEM FOR DENTAL BLEACHING

This application claims the benefit of U.S. Provisional Patent Application Serial No. 60/065,924 filed on Nov. 17, 1997.

BACKGROUND OF THE INVENTION

The invention relates to devices and methods for delivering a dental bleach from an unmixed state in a container to a mixed state on a patient's teeth in a single unified step. More particularly, the invention relates to a binary or n-ary dispenser which serves to contain the constituents of a dental bleach for long term storage, which serves to mix the constituents of the bleach in the appropriate proportions, and which serves to dispense quantities of the correctly mixed bleach directly onto a patient's teeth.

THE PRIOR ART

Historically the bleaching of teeth has typically been accomplished with peroxides, either hydrogen peroxide or carbamide peroxide. The peroxide may be applied to the patient's teeth in a dental office, and heat may then be applied to the peroxide to cause release of oxygen radicals which carry out the bleaching process. Heat was often applied to the peroxide using heat guns or lamps. As it was also well known that light decomposes peroxides, high intensity light from conventional dental light sources, such as those used to cure dental composites, were also utilized to directly activate peroxides. As lasers have replaced conventional light sources in dental offices, lasers have been used to activate peroxide both directly and indirectly. It is also well known that peroxides can be decomposed by use of basic compounds such as calcium hydroxide or sodium hydroxide.

Chemically, peroxides give up a free radical oxygen atom when activated by an appropriate light source or chemical compound. Once released in the vicinity of teeth, the free radical oxygen atom attacks the carbon—carbon bonding structure of the organic molecule producing the stain. The offending molecule is oxidized and the oxygen is reduced. The liberation of free radical oxygen can be performed by increasing the energy level of the peroxide molecule by adding energy to it or by chemically pushing the peroxide solution to a basic pH number. When there is an excess of hydroxy anion (OH) present, the proton (H) ion is abstracted from the peroxide. Once the peroxide is missing the proton that it gave to the hydroxy ion, the peroxide molecule must give up a free radical oxygen. Thus, the reaction allowing release of stain-removing oxygen can be driven chemically. Chemical activation, light activation and heat activation have been conduced simultaneously to speed up the release of oxygen radicals.

If a material intended to be used to bleach teeth is stored with peroxide in it, the peroxide will decompose and its effectiveness will be lost. Therefore it is preferable to mix the peroxide with the other materials of the dental bleach immediately prior to bleaching. Historically this has been accomplished by supplying a dentist with a variety of containers having the constituents of the dental bleach, requiring the dentist to measure a specified amount of each constituent and mix them at chairside before bleaching a patient's teeth. That was undesirable due to the time required and the potential for human error. A need for an improved system was evident.

OBJECTS OF THE INVENTION

It is an object of the invention to provide a dental bleach storage, mixing and delivery device that includes a storage area where the constituent components of a dental bleach may be stored separately from each other. In the preferred embodiment of the invention, the invented apparatus features a syringe with two (or more) barrels, a first barrel containing a peroxide and the second barrel containing bleach constituents to be mixed with the peroxide.

It is an object of the invention to provide a dental bleach storage, mixing and delivery device that automatically mixes constituents of a dental bleach while dispensing those components from storage to a patient's teeth. It is a feature of the invention that the constituents of a dental bleach will be transported from a storage area in the preferred syringe and through a mixing tip which mixes the components, from which the mixed bleach is released to a patient's teeth.

It is an object of the invention to provide a dental bleach storage, mixing and delivery device that transports unmixed constituents of a dental bleach from a storage area directly to a patient's teeth in the form of a mixed bleach without any intermediate steps where human error could be introduced. It is a feature of the invention that the constituents of a dental bleach will be transported directly from a storage area in the preferred syringe and through a mixing tip which mixes the components and then directly to a patient's teeth in a single motion and without interruption.

Additional objects, features and advantages of the invention will become apparent to persons of ordinary skill in the art upon reading the specification in light of the attached drawings.

BRIEF DESCRIPTION OF THE DRAWING

FIG. 1 depicts one preferred embodiment of a dental bleach storage, mixing and delivering device according to the invention.

DETAILED DESCRIPTION OF PREFERRED EMBODIMENTS

A. Structure of the Preferred Binary Energizer

Referring to FIG. 1, a depiction of one preferred embodiment of the invention is provided. Depicted is a preferred binary dental bleach storage, mixing and delivery device 101. The preferred device 101 is binary in that it has two separate storage chambers because when the preferred dental bleaching formulas are used, only two storage chambers are required. With other dental bleaching formulas, however, a different number of storage chambers may be used (from 2 to n, where n is an integer), yielding an n-ary dental bleach storage, mixing and delivery device.

The preferred device 101 is configured generally in the form of a syringe. The device 101 includes a barrel 102 having a proximal end 102a and a distal end 102b. A longitudinally reciprocating plunger 103 is shown protruding from the barrel 102 at its proximal end 102a. The barrel 102 is divided into separate, sealed storage compartments, being labelled as first storage compartment 104a and a second storage compartment 104b. The storage compartments are sealed with respect to each other during storage so that a constituent of a dental bleach in one storage compartment will not contact or otherwise interact with the other storage compartment.

The preferred plunger 103 depicted includes a handle 103c at its proximal end against which a dentist will apply a force in order to cause the plunger 103 to travel longitudinally in the barrel 102 toward the distal end 102b of the barrel. The plunger includes a first rod 103a and a second rod 103b. At the distal end of each rod 103a and 103b, a seal 103d and 103e is located. The seals 103d and 103e are located within the barrel storage compartments 104a and 104b respectively and serve to create a dynamic seal with the interior walls of the compartments 104a and 104b so that when constituents of a dental bleach are being stored in the compartments 104a and 104b, there is no leakage past the seals 103d and 103e toward the proximal end of the barrel 102, and so that when the plunger 103 is moved in a sliding motion within the chambers 104a and 104b toward the distal end 102b of the barrel, any dental bleach within the storage chambers 104a and 104b are forcibly transported within the interior of the chambers 104a and 104b toward the barrel distal end 102b by the dynamic sealing action of the seals 103d and 103e within the chambers 104a and 104b. Each chamber 104a and 104b has an exit orifice 104c and 104d respectively through which constituents of a dental bleach will exit the chambers during use of the device 101. Ordinarily the barrel 102 will be fitted with a cap (not shown) for storage and the mixing tip 106 will be installed immediately prior to use.

At the distal end 102b of the barrel 102, a staging area 105 within the barrel 102 is located. As constituents of a dental bleach are expelled from their respective chambers, they first join in the staging area 105 before passing through the exit orifice 106 of the barrel 102 and into a mixing tip 106. The mixing tip 106 is preferably a commercially available mixing tip that will uniformly and thoroughly mix the contents of chambers 104a and 104b to create a finished dental bleach. The finished dental bleach exiting the mixing tip will then be applied directly to a patient's teeth.

From the above structural description, it can be seen that constituent components may be stored indefinitely in chambers 104a and 104b, but may be readily and easily mixed by a dentist at chairside for direct and immediate application to the teeth of a patient. The dentist need only depress the plunger handle 103c and the structure of the device 101 ensures mixing of the constituents of the dental bleach in the correct proportions with possibility of human error. The chambers 104a and 104b may have the same or different volumes. It is anticipated that the chambers will usually have different volumes in order to accommodate the exact ratio of Peroxide and Basic Element that must be used for optimal dental bleaching.

An alternative but less formal description of the preferred device depicted as 101 is a double barreled syringe. Preferably, the syringe will have an aqueous solution of peroxide in an appropriate medium contained with a first chamber of the barrel (the "Peroxide"), and an aqueous solution of a chemically basic element preferably in the same medium as the first chamber (the "Basic Element"). Depressing the plungers causes the two aqueous solutions (the Peroxide and the Basic Element) to mix in the mixing tip and to be deliverable out of the mixing tip to a patient's teeth.

Each or both of the chambers could also contain other elements or ingredients useful or beneficial in the reaction that causes release of oxygen radicals from the Peroxide. For example, dyes, stains, particles or colorants could be added to the mediums to absorb specific wavelengths of light (e.g., orange to absorb blue-green wavelengths of 400–500 nanometers; and blue-green to absorb near infra-red wavelengths of 1064 nanometers). The purpose of the dyes, stains, particles or colorants is to absorb specific wavelengths of light so that the light energy may accelerate release of oxygen radicals from the peroxide molecules. Inert crystals may also be added to one or both of the mediums to absorb specific wavelengths of light and transfer the energy to the peroxide molecule. Indicators may be added to one or both mediums to provide a visual indication of when the reaction causing release of oxygen radicals from the peroxide is complete. These various additives would be placed either in the medium with the Peroxide or with the Basic Element depending on reactivity of the additives with the other components of the Peroxide and the Basic Element.

Another feature of the invention is that the concentration of the peroxide may be diluted while mixing it with the Basic Element. It has been found that volumetric concentrations of hydrogen peroxide in excess of 35% are very effective for in-office bleaching procedures, but concentrations above 50% have been shown to cause post procedure pain and resorption of the pulpal tissues. To accommodate a 35% hydrogen peroxide mix, the following syringe system may be implemented: Chamber 104a can be sized to contain 10 milliliters of bleaching constituent, and chamber 104b can be sized to contain 4.3 milliliters of a chemical base solution, then when the two are mixed, a 35% concentration of peroxide is achieved.

The preferred volumes of the chambers 104a and 104b are 5.0 ml. and 2.15 ml. respectively, and the preferred ratio of the volume of chamber 104a to 104b is in the range of 1:1 to 1:10.

Preferably, the barrel is made from polypropylene although it could be constructed from any non-reactive polymer. The preferred plunger rod 103b is made from polypropylene although it could be constructed from any non-reactive polymer. The preferred handle 103c is made from polypropylene although it could be constructed from any non-reactive polymer. The preferred seals 104d are made from silicone compounds as are known in the art to be useful for seal construction although they could be constructed from any flexible non-reactive polymer or other material.

Suitable mixing tips for use in the invention include a series of small tips available from the 3M Corporation of St. Paul. Minn. Mixing tips are also available from Plas-Pak Industries, Inc. of Norwich, Conn. Preferably, the mixing tip will have complete mixing capabilities and compact length (less than one inch in length will be preferred if available).

Syringe barrels and plungers usable in the invention are commercially available from Plas-Pak Industries, Inc. of Norwich, Conn. They are generally referred to as two component cartridge systems. Commercially available volumes from Plas-Pak include 3 cc. to 60 cc. in which a ratio of one chamber to the other is from 1:1 to 10:1 (e.g., for a 10:1 ratio system, ten parts of one component would be dispensed for one part of another). Custom made two component systems can be ordered from Techcon Systems, Inc. of Carson, Calif.

As described above, it is contemplated that the plunger will be sized to fit in a dentist's hand and dispense a single dose of whitener. However, larger mixing systems could be constructed using the inventive idea. Also, a dispensing gun could be constructed that would receive the dental bleach storage, mixing and delivery device 101 and when squeezed would apply an equal force to both plungers in order to force whitener through the mixing tip to the patient.

B. Preferred pH Levels

If the pH level of the Basic Element is too high, rapid or immediate decomposition of the peroxide will occur. Rapid decomposition of the peroxide results in the majority of the oxygen radicals produced combining with each other to form molecular oxygen ($O_2$). The pH should be selected to be at a level that produces sufficient concentrations of oxygen radicals to carry out effective bleaching without losing a significant amount of oxygen radicals to the formation of molecular oxygen. To achieve this, the pH should be selected to be at a level that causes controlled decomposition of the peroxide over an optimal time frame. Preferably, the pH will be selected to be in the range of 0.75 to 11, although the invention may be employed even if the pH is outside this range. More preferably, the pH will be in the range of 9 to 9.5. As pH is increased above 9.5, the rate of decomposition increases to the point that a large amount of oxygen free radicals will be lost to formation of molecular oxygen. As pH is reduced below 9, the rate of decomposition of the peroxide slows to the point that the time saving advantage of chemically induced peroxide decomposition is lost.

C. Chemical Constituents

Agents that can be used to adjust pH to the desired level include but are not limited to: sodium hydroxide, sodium carbonate, sodium bicarbonate, calcium hydroxide, calcium carbonate, calcium bicarbonate, magnesium hydroxide, magnesium carbonate, magnesium bicarbonate, urea and various urea derivatives. The preferred agents for setting pH levels are sodium hydroxide, calcium carbonate and calcium bicarbonate, although others could be used while implementing the invention.

The amount of agent needed to set the desired pH level can be determined from the equation: $pH=-\log[H_3O^+]$. The concentration of the hydronium ion ($[H_3O^+]$) is calculated using a dissociation constant $K_a$. Once the desired pH is decided, the appropriate concentration can be calculated. The appropriate concentration will be different for each of the chemicals listed above because they each have a different course of the chemical reaction, the pH will decrease as the Basic Element is consumed.

Other pH regulating mixtures, such as buffering agents, can be used. Buffering agents are combinations of bases (which tend to raise pH) or acids (which tend to lower pH) and their salts. Buffers are typically intended to maintain a specific pH although chemistry which would tend to change pH is taking place. Buffers are available for any desired pH level and are commercially available from common chemical suppliers. One buffer usable with the invention is pH 9 buffer, catalog number E-05977-16 available from Cole-Parmer of Vernon Hill, Ill. In some instances, it may be preferred to use a buffer that resists pH change rather than basic chemicals for ease of use and to resist pH change and maintain desired pH for a greater length of time.

Peroxides usable with the invention include but are not limited to hydrogen peroxide, carbamide peroxide, calcium bicarbonate peroxide and sodium bicarbonate peroxide. Hydrogen peroxide is preferred for its economy and ease of use.

The medium used to carry the peroxide could be anhydrous gelatin, fumed silica, other silica derivatives, hydroxyethylcellulose, lanolate palmitate, oleate, sodium lauryl sulfate, sodium sterate, calcium stearate, and/or plasticizing agents such as those common to dental bleaching products. The preferred medium is anhydrous gelatin.

D. Additives

Either the Basic Element or the Peroxide may include additives to achieve desired performance characteristics in a whitener. For example, some additives may be used to make the composition more effective at whitening for a particular application, or to make the mixture more palatable to the patient.

In applications where the dentist will provide the bleaching system to the patient for home use, it may be desirable to add flavoring such as fruit or mint to make the mixture palatable. The nature of the invention makes this possible. It is known that the Peroxide will react with organic molecules and that is how it caries out dental bleaching. If organic molecules, such as a flavoring, are added to the Peroxide, both the flavoring and the Peroxide will degrade in storage. Instead, flavoring may be mixed with the Basic Element where it will not react and will only be exposed to Peroxide immediately before application to the patient's teeth. Alternatively, a third storage chamber could be provided that contains flavoring to be mixed with the Basic Element and the Peroxide immediately before application to the patient's teeth.

For convenience, it may be desirable to include a chemical indicator that will let the dentist or patient know when the potency of the peroxide is gone. Such indicators usually operate by detecting changes in pH. Such indicators are usually a first color at a first pH level and change to a second different color at another pH level, thereby indicating a pH change. For example, Thymol Blue (catalog nuber 31,959-7 from Aldrich Chemicals of Milwaukee, Wis.) is a commonly used pH indicator. It is blue at basic pH but turns yellow at neutral pH (pH=7). At acidic pH it will turn red. As with flavoring, it is desirable to keep the indicator separate from the Peroxide until use in order to avoid degradation and retain potency.

It may be desirable to include dye in the dental bleaching composition. Dye may be used to absorb light, which will generate heat and accelerate decomposition of the peroxide, speeding whitening of the teeth. An example of a dye usable with the invention Is betacarotene. Betacarotene is a complex organic molecule that is orange in color. Orange absorbs light in the blue to blue/green wavelength range (400–550 nanometers). Betacarotene is a convenient dye for dentists because their offices are typically already equipped with a curing light which generates blue to blue/green light. Utilization of betacarotene and other orange dyes is therefore preferred for absorbing light, creating heat, accelerating decomposition of the Peroxide and speeding whitening in the invention due to its convenience, although other color dyes could be used as well.

It is important to keep the dye (an organic molecule) separate from the Peroxide until immediately prior to application of the whitening mixture to the patient's teeth, otherwise the Peroxide will tend to break down and lose its effectiveness during storage. Instead of dye, inert colored material could be used to absorb light of a desired wavelength and create heat for use in the whitening process. For example, colored glass beads or fumed silica could be incorporated into the whitening composition to absorb light and create heat. Adding particles such as colored glass, fumed silica or others will also tend to thicken the composition. Use of inert additives such as this enables them to be mixed with either the Peroxide or the Basic Element.

E. Prophetic Examples

Below, four (4) examples usable with the invention are provided. It is believed that when implemented, the examples will be usable and effective.

EXAMPLE 1

A double barrel syringe is provide with a first chamber having a volume of 4 cc. and the second chamber having a volume of 1 cc. 50% hydrogen peroxide is added to an anhydrous gelatin until saturated. 0.40 grams of 50 micron diameter orange glass beads per cc. of gelatin/hydrogen peroxide are added to the mixture and placed in the first chamber. 0.187 mole/liter sodium hydroxide is added to the anhydrous gelatin until saturated and this mixture is placed in the second chamber. The plungers are placed in the syringe barrels and a 1.5 inch mixing top is placed at the dispensing end of the syringe.

At chairside, the dentist prepares the patient for treatment. He then applies the mixture of components from the first and second chambers of the syringe as mixed by the mixing tip to the patient's teeth. As the material passes through the mixing tip, sodium hydroxide is thoroughly and automatically mixed with the hydrogen peroxide/glass bead mixture, resulting in a whitener that is referred to as "energized". This mixing process will also reduce the hydrogen peroxide concentration from 50% to 35–40%, a more desirable range for use in teeth whitening.

Next, the dentist will apply a visible blue to blue/green light (with a wavelength in the approximate range of about 450 nanometers to 550 nanometers to the energized whitener. The orange glass beads will absorb the light and as a result will heat up. The heat is transferred from the beads to the surrounding mixture, including the peroxide. The energized hydrogen peroxide then oxidizes the offending molecules causing stains or discoloration on the patient's teeth. Finally, the dentist may store the unused portion of the syringe without loss of potency for later use.

EXAMPLE 2

A double barrel syringe is provide with a first chamber having a volume of 4 cc. and the second chamber having a volume of 1 cc. 50% hydrogen peroxide is added to an anhydrous gelatin until saturated and placed in the first chamber. A 0.187 mole/liter sodium hydroxide and betacarotene solution (about 0.25 gram of betacarotene) is prepared and added to the anhydrous gelatin until saturated and this mixture is placed in the second chamber. The plungers are placed in the syringe barrels and a 1.5 inch mixing top is placed at the dispensing end of the syringe.

At chairside, the dentist prepares the patient for treatment. He then applies the mixture of components from the first and second chambers of the syringe as mixed by the mixing tip to the patient's teeth. As the material passes through the mixing tip, sodium hydroxide is thoroughly and automatically mixed with the hydrogen peroxide mixture, resulting in a whitener that is referred to as "energized". This mixing process will also reduce the hydrogen peroxide concentration from 50% to 35–40%, a more desirable range for use in teeth whitening.

Next, the dentist will apply a visible blue to blue/green light (with a wavelength in the approximate range of about 450 to 550 nanometers to the energized whitener. The orange betacarotene will absorb the light and as a result will heat up. The heat is transferred to the surrounding mixture, including the peroxide. The energized hydrogen peroxide then oxides the offending molecules causing stains or discoloration on the patient's teeth. Finally, the dentist may store the unused portion of the syringe without loss of potency for later use.

EXAMPLE 3

A double barrel syringe is provide with a first chamber having a volume of 2 cc. and the second chamber also having a volume of 2 cc. 20% carbamide peroxide is added to an anhydrous gelatin until saturated and placed in the first chamber. A pH 9 buffer solution (such as catalog number E-05977-16 from Cole-Parmer Company of Vernon Hills, Ill.) is prepared with about half the water recommended or at twice the recommended strength. The buffer is added to anhydrous gelatin until saturated and the mixture is placed in the second chamber. The plungers are placed in the syringe barrels and a 1.5 inch mixing top is placed at the dispensing end of the syringe.

The patient then dispenses the whitener from the syringe through the mixing tip and into a mouth guard type of whitening tray for use outside of a dental office. As the material passes through the mixing tip, the carbamide peroxide is thoroughly and automatically mixed with the buffer, diluting the buffer by 50% and bringing it to the recommended concentration, resulting in a whitener that includes energized carbamide peroxide. This mixing process will also reduce the carbamide peroxide concentration to about 10%, which is the widely accepted concentration as being both safe and effective. The patient then places the tray with whitener on his teeth for about one hour. Finally, the patient may store the unused portion of the syringe without loss of potency for later use.

EXAMPLE 4

A double barrel syringe is provide with a first chamber having a volume of 2 cc. and the second chamber also having a volume of 2 cc. 10% hydrogen peroxide is added to an anhydrous gelatin until saturated and placed in the first chamber. A pH 9 buffer solution (such as catalog number E-05977-16 from Cole-Parmer Company of Vernon Hills, Ill.) is prepared with about half the water recommended or at twice the recommended strength. The buffer is added to anhydrous gelatin until saturated and the mixture is placed in the second chamber. The plungers are placed in the syringe barrels and a 1.5 inch mixing top is placed at the dispensing end of the syringe.

The patient then dispenses the whitener from the syringe through the mixing tip and into a mouth guard type of whitening tray for use outside of a dental office. As the material passes through the mixing tip, the hydrogen peroxide is thoroughly and automatically mixed with the buffer, diluting the buffer by 50% and bringing it to the recommended concentration, resulting in a whitener that includes energized hydrogen peroxide. This mixing process will also reduce the hydrogen peroxide concentration to about 5%, which is the widely accepted concentration as being both effective and safer than a 10% concentration. The patient then places the tray with whitener on his teeth for about one hour. Finally, the patient may store the unused portion of the syringe without loss of potency for later use.

The foregoing description and drawings are illustrative of preferred embodiments of the invention and are not intended to be limiting of the invention's scope. The scope of the invention is defined by the appended claims, which should be interpreted to cover that which is disclosed herein and equivalents thereof.

What is claimed is:

1. A method for preparing a dental whitener for application to a patient's teeth comprising the steps of:
   selecting a syringe that includes:
   a barrel having a proximal and a distal end,
   a first chamber located in said barrel,
   a second chamber located in said barrel,
   a plunger having a proximal end, a distal end, and a body therebetween, said plunger being reciprocally slidable within said barrel,
   a plunger handle being located at said plunger proximal end, a first and a second plunger seal, each of said first and second plunger seals being located at said plunger distal end, a mixing tip installed at said barrel distal end, a peroxide located in said first chamber, and a basic element located in said second chamber, depressing said plunger, thereby forcing a quantity of peroxide from said first chamber and a quantity of basic element from said second chamber through said mixing tip where they are mixed together to form a dental whitener, applying said dental whitener to a patient's teeth, applying a light source to said dental whitener on said patient's teeth so that light energy is absorbed by said whitener, said whitener generating heat as a result of absorbing light energy, said heat causing release of oxygen ions from said peroxide, and said oxygen ions acting to whiten the patient's teeth.

2. A method as recited in claim 1 wherein said basic element comprises a component selected from the group consisting of sodium hydroxide, calcium carbonate and calcium bicarbonate.

3. A method as recited in claim 1 wherein said peroxide is selected from the group consisting of carbamide peroxide, calcium bicarbonate peroxide, sodium bicarbonate peroxide and hydrogen peroxide.

4. A method as recited in claim 1 wherein said basic element has a pH in the range of about 7 to 11.

5. A method for whitening teeth in an home environment comprising the steps of:

selecting a syringe that includes:

a barrel having a proximal and a distal end, a first chamber located in said barrel, a second chamber located in said barrel, a plunger having a proximal end, a distal end, and a body therebetween, said plunger being reciprocally slidable within said barrel, a plunger handle being located at said plunger proximal end, a first and a second plunger seal, each of said first and second plunger seals being located at said plunger distal end, a mixing tip installable at said barrel distal end, a peroxide located in said first chamber, and a basic element located in said second chamber, depressing said plunger, thereby forcing a quantity of peroxide from said first chamber and a quantity of basic element from said second chamber through said mixing tip where they are mixed together to form a dental whitener, applying said dental whitener to a tooth, allowing the whitener to remain on the tooth for a desired time period so that oxygen ions may be released from said whitener, contact, the tooth and exert a whitening effect on it.

6. A method as recited in claim 5 further comprising the step of placing said dental whitener into a tray and placing said tray into a person's mouth where presence of whitener in said tray will cause said whitener to contact at least one tooth.

7. A method as recited in claim 6 wherein said whitener is permitted to remain in contact with a tooth for about one hour.

8. A method as recited in claim 5 wherein said peroxide is selected from the group consisting of carbamide peroxide, calcium bicarbonate peroxide, sodium bicarbonate peroxide and hydrogen peroxide.

* * * * *